United States Patent [19]
Göttfert

[11] Patent Number: 5,992,248
[45] Date of Patent: Nov. 30, 1999

[54] APPARATUS FOR DETERMINING THE MECHANICAL DEFORMATION BEHAVIOR OF EXTRUDABLE MEASURING SAMPLES

[75] Inventor: Axel Göttfert, Buchen, Germany

[73] Assignee: Göttfert Werkstoff-Prüfmaschinen GmbH, Buchen, Germany

[21] Appl. No.: 09/038,446

[22] Filed: Mar. 11, 1998

[30] Foreign Application Priority Data

Mar. 11, 1997 [DE] Germany ............... 197 09 989

[51] Int. Cl.$^6$ ................................. G01N 33/00
[52] U.S. Cl. ..................... 73/866; 73/824; 425/324.1
[58] Field of Search ............. 73/866, 863, 822, 73/823, 824, 159, 54.01, 54.11, 54.14; 264/176.1, 165; 425/324.1, 328, 376.1

[56] References Cited

U.S. PATENT DOCUMENTS

| | | | |
|---|---|---|---|
| 2,986,778 | 9/1961 | Goodwin et al. | 19/98 |
| 4,116,601 | 9/1978 | Lehmann et al. | 425/324.1 |
| 4,597,731 | 7/1986 | Suzuki | 425/204 |
| 5,607,703 | 3/1997 | Sakai et al. | 264/176.1 |

FOREIGN PATENT DOCUMENTS 1 904 079  1/1969  Germany.

*Primary Examiner*—Hezron Williams
*Assistant Examiner*—Thuy Vinh Tran
*Attorney, Agent, or Firm*—Alston & Bird LLP

[57] ABSTRACT

An apparatus for determining the mechanical deformation behavior of extrudable measuring samples and which has two drivable take-up rollers (2) disposed pairwise on a resiliently deflectable mounting frame, to which an extruded measuring sample billet is supplied. In order to prevent the adhesion of the measuring samples on the take-up rollers (2), a drivable guidance device for the measuring sample is mounted on the resilient frame downstream of the takeup rollers (2). The drivable guidance device comprises two drivable guidance cylinders (5).

16 Claims, 1 Drawing Sheet

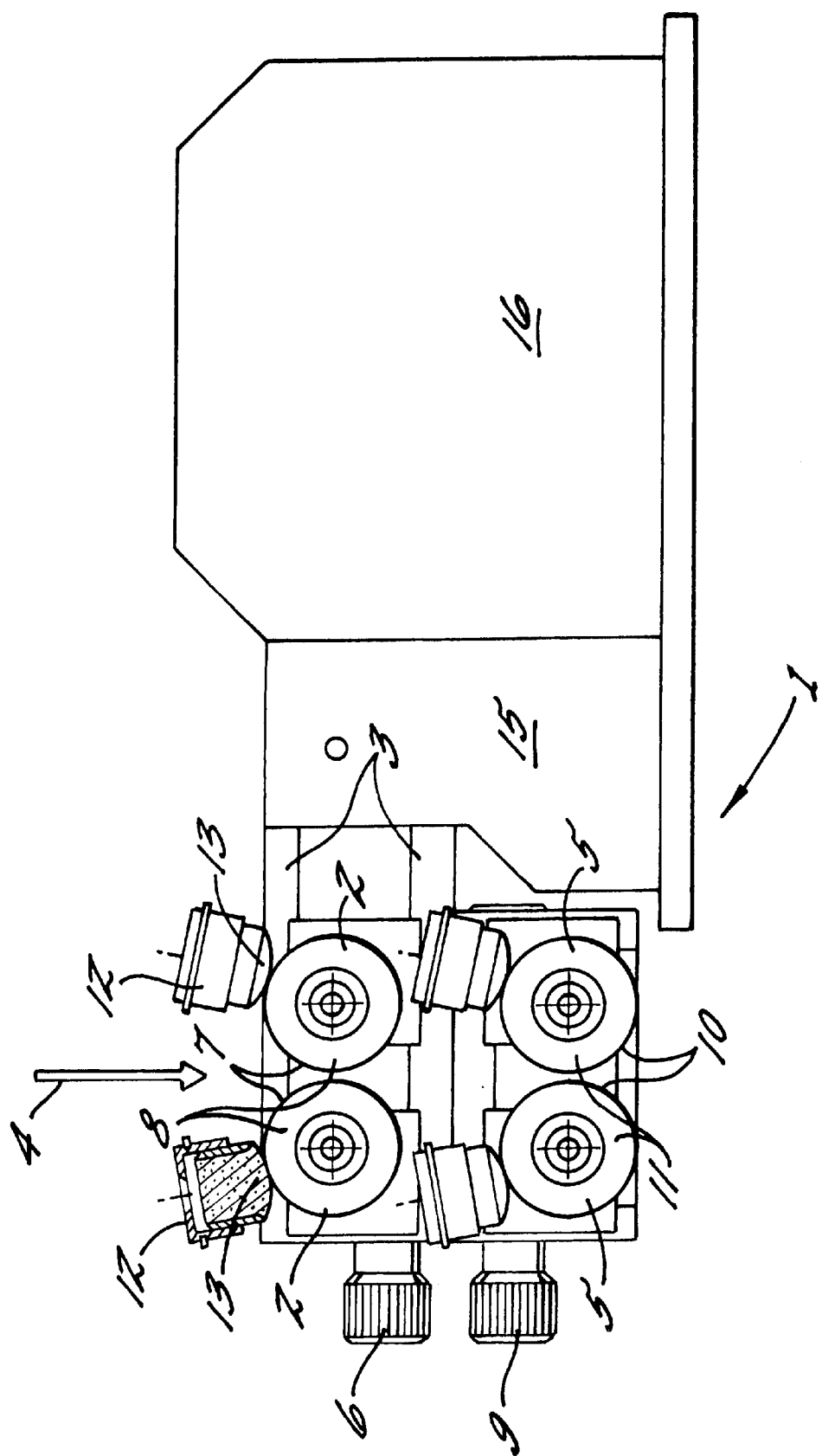

ized polymers, such as for example polypropylene (PP), polycarbonate (PC) and polyamide (PA), the polymer billet adheres to the take-up rollers which can be traced back to the pronounced "sticking effect" of these polymers in the melt state. This sticking effect not only occurs when the polymer billet is guided between the take-up rollers but rather also when the polymer billet is guided in front of the rotating take-up rollers, thus, across the front faces of the take-up rollers, wherein the extruded measuring sample billet is elongated across the touching contact at the rotating front faces.

APPARATUS FOR DETERMINING THE MECHANICAL DEFORMATION BEHAVIOR OF EXTRUDABLE MEASURING SAMPLES

BACKGROUND OF THE INVENTION

The present invention relates to an apparatus for determining the mechanical deformation behavior of extrudable measuring samples, wherein two drivable take-up rollers are disposed pairwise on a resiliently deflectable mounting arrangement, and to which an extruded measuring sample billet is supplied.

Such apparatus, which are commonly called extension testers, are utilized in synthetic material processing where the maximum extensibility and the tensile strength of the synthetic material melts are determined in order to determine the highest possible processing speed. For this purpose an extruded measuring sample billet is supplied to a take-up apparatus having a pair of take-up rollers, and the sample billet is continuously elongated at continuously increasing take-up speed. The bearing force exerted in the process onto the pair of take-up rollers is measured and drawn on for evaluating the tensile strength at tearing of the measuring sample billet.

DE 19 04 079 describes an apparatus for determining the mechanical deformation behavior of extruded measuring samples, which comprises a pair of take-up rollers drivable at a variable rotational speed and which are resiliently supported in the direction of transport of the measuring sample. The take-up rollers are for that purpose mounted on a resiliently supported carrier. To determine the mechanical deformation behavior of a measuring sample, the deflecting force acting at given rotational speed of the take-up rollers on to the take-up rollers, respectively the support, is measured continuously.

The take-up rollers often have a corrugated or indented surface in order to prevent the measuring sample billet from slipping through while it is being pulled out. As a rule, the measuring sample billet has a cross section between 2 mm and 3 mm and, during the pulling-out between the take-up rollers, is rolled out to approximately 1 mm.

The use of the known extension tester is frequently problematic in practice since in the case of a large portion of the conventionally used polymers, such as for example polypropylene (PP), polycarbonate (PC) and polyamide (PA), the polymer billet adheres to the take-up rollers which can be traced back to the pronounced "sticking effect" of these polymers in the melt state. This sticking effect not only occurs when the polymer billet is guided between the take-up rollers but rather also when the polymer billet is guided in front of the rotating take-up rollers, thus, across the front faces of the take-up rollers, wherein the extruded measuring sample billet is elongated across the touching contact at the rotating front faces.

It is an object of the present invention to provide an apparatus for determining the mechanical deformation behavior of extrudable measuring samples of the type under consideration, and to develop it further such that the adhesion of the measuring sample billet on the take-up rollers is as much as possible avoided and, in particular, is avoided for measuring samples with low viscosities.

SUMMARY OF THE INVENTION

The above and other objects and advantages of the present invention are achieved by the provision of an apparatus which comprises two drivable take-up rollers disposed pairwise on a resiliently deflectable mounting frame to which an extruded measuring sample billet is supplied. In addition, a drivable guidance device for the measuring sample billet is mounted downstream of the take-up rollers in the direction of take-up of the extruded measuring sample billet.

It has been found according to the invention that the melts of interest in this connection when passing the take-up roller configuration become immediately solidified due to the contact with the take-up rollers. The quasi-extruded measuring sample billet can therefore, at the beginning of the measurement, for example manually, be supplied to a guidance device without problems. It was further found according to the invention that a gumming-up of the take-up rollers can be avoided simply if the guidance device is drivable when the measuring sample billet is actively guided away from the take-up rollers so that it cannot become wound about the take-up rollers. Due to the advanced solidification of the measuring sample billet the gumming-up of the guidance device can be avoided.

In an especially advantageous variant of the arrangement according to the invention, means are provided for synchronizing the driving of the guidance device with the driving of the take-up rollers. The measuring sample billet should in any case be carried off the guidance device at least as fast as it is taken up by the take-up rollers. In order to reliably prevent the building-up of the measuring sample billet after it has passed the take-up rollers, the guidance device could also be driven slightly faster than the take-up rollers.

The guidance device is especially effective if it is disposed in the immediate proximity of the take-up rollers. It is therefore suggested that the guidance device be disposed directly or indirectly on the mounting frame for the take-up rollers. It has additionally been found to be advantageous in this connection if the guidance device is optionally mountable so that it can be mounted only in the event of its actual use. In addition, in that case conventional extension testers with a guidance device can also be retrofitted.

There are different possibilities for realizing the guidance device. In a variant which from a structural point of view is especially advantageous, since it is simple, the guidance device comprises at least two drivable guidance cylinders disposed in pairs. Within the scope of the apparatus according to the invention, the guidance cylinders can be disposed such that the measuring sample billet is guided between the running surfaces of the guidance cylinders or such that the measuring sample billet is guided on the front faces of the guidance cylinders.

As already explained above, it is advantageous to synchronize the driving of the guidance cylinders with the drive of the take-up rollers which can be attained simply through a coupling, for example in the form of a gearing. For example, the driving shaft of the take-up rollers can be connected through a gearing connection with the driving shaft of the guidance cylinders. The transport speed of the guidance cylinders should under no circumstances be lower than the transporting speed of the take-up rollers. It is of advantage to select the transporting speed of the guidance cylinders to be slightly higher than the transporting speed of the take-up rollers in order to prevent the measuring sample billet from building up.

The undesirable adhesion of the measuring sample billet on the take-up rollers can be traced to the fact that the adhesion force $F_K$ is greater at the take-up rollers than the detachment force $F_A$ of the melt from the take-up rollers. In the event of adhesion thus $F_K > F_A$. With the aid of the drivable guidance device, suggested according to the invention, this relationship can be reversed so that $F_K < F_A$.

In an especially advantageous variant of the apparatus according to the invention, not only the detachment force $F_A$ is increased with the air of a drivable guidance device but the adhesion force $F_K$ is also decreased. To that end means are provided for wetting the surfaces of the take-up rollers coming into contact with the measuring sample billet. When a suitable wetting agent is selected, a vapor film is formed on the surface of the take-up rollers concomitant with evaporative cooling. The vapor film as well as also the cooling counteract the adhesion of the melt on the take-up rollers.

In specific cases, i. e. with certain measuring sample materials, it can additionally be of advantage to provide on the guidance cylinders corresponding means for also wetting the surfaces which come into contact with the measuring sample billet.

Maintenance of the means for wetting should be as simple as possible. It is therefore suggested to assign to each take-up roller, and to each guidance cylinder, a reservoir for a wetting agent with each reservoir being in contact with the particular surface to be wetted. This could be attained in simple manner with the aid of a correspondingly disposed textile structure with absorptive capacity or a small sponge.

The wetting agent must in any event be compatible with the measuring sample material. In view of a rapid and reliable formation of a vapor film, it is suggested to use a readily volatile liquid, for example an alcohol, as the wetting agent.

Since the means for wetting the surfaces of the take-up rollers and in particular the reservoir for the wetting agent, as a rule, will also be disposed directly or indirectly on the mounting frame for the take-up rollers, the evaporation of the wetting agent leads to a reduction of the weight of the total arrangement mounted on the mounting frame. The weight loss therefore results in inaccurate measuring results. To compensate for this measuring value inaccuracy, it is suggested to provide means for detecting the weight loss due to the evaporation of the wetting agent.

BRIEF DESCRIPTION OF THE DRAWING

There are different possibilities for implementing and further developing the teaching of the present invention in an advantageous manner. For this purpose, reference is made to the subsequent explanation of a specific preferred embodiment of the invention when considered in conjunction with the accompanying drawing, which is a side view of a preferred embodiment of an apparatus according to the invention for determining the mechanical deformation behavior of an extrudable measuring sample.

DETAILED DESCRIPTION OF THE PREFERRED EMBODIMENT

The sole drawing FIGURE illustrates an apparatus 1 for determining the mechanical deformation behavior of extrudable measuring samples in accordance with the present invention. The apparatus 1 comprises two take-up rollers 2 disposed pairwise, and which are disposed on a resiliently deflectable mounting frame, which as illustrated takes the form of a balance beam 3. The balance beam 3 is in turn supported by a carrier 15 which is part of a housing 16 which may enclose the controls of the apparatus 1. The controls include a suitable means for determining the force exerted on the take-up rollers 2. To the take-up rollers 2 is supplied an extruded measuring sample billet, which is indicated by an arrow 4. The take-up rollers 2 are drivable under regulation so that the measuring sample billet can be elongated for example with continuously increasing take-up speed.

According to the invention a drivable guidance device for the measuring sample billet is provided downstream of the take-up rollers 2 in the direction of take-up. In the embodiment depicted, this guidance device comprises two drivable guidance cylinders 5 disposed in pairs. The guidance cylinders 5 are also mounted on the balance beam 3.

With the aid of a screw 6, the spacing between the two take-up rollers 2 can be varied so that, depending on the disposition of the take-up rollers 2, the measuring sample billet can be guided either between the running surfaces 7 or across the front faces 8 of the take-up rollers 2. Correspondingly, with the screw 9 the spacing between the two guidance cylinders 5 can be varied. The measuring sample billet can thus be guided either between the running surfaces 10 or over the front faces 11 of the guidance cylinders 5. Essential in connection with the present invention is only that the measuring sample billet comes into contact with the take-up rollers 2 as well as also with the guidance cylinders 5.

The driving of take-up rollers 2 and the driving of guidance cylinders 5 are synchronized which may be realized through a coupling in the form of a gearing not further denoted. In order to prevent having the measuring sample billet build up after it passes the take-up rollers 2, the transport speed of the guidance cylinders 5 is slightly higher than the transport speed of the take-up rollers 2.

The apparatus 1 depicted in the sole FIGURE is additionally provided with means for wetting the surfaces which come into contact with the measuring sample billet, here the running surfaces 7 of the take-up rollers 2 and the running surfaces 10 of the guidance cylinders 5. The means for wetting comprises for each take-up roller 2, and for each guidance cylinder 5, a reservoir 12 for a wetting agent. Each reservoir 12 is in contact via a small sponge 13 with the particular surface to be wetted. A readily volatile alcohol, such as for example ethanol, may be used as the wetting agent.

To determine the mechanical deformation behavior of a measuring sample, the force exerted during the extension of the measuring sample onto the balance beam 3 is determined. In addition, the weight loss due to the continuous evaporation of the wetting agent, of the total arrangement mounted on the balance beam 3, is determined. Within the scope of a measuring value evaluation, the measuring value inaccuracy which can be traced back to the weight loss, can accordingly be corrected.

In conclusion, it will be understood that the present invention is not limited to the specific features of the above described embodiment, and although specific terms are employed, they are used in a generic and descriptive since only and not for purposes of limitation. Also, not all of the described features are necessary for the successful practice of the invention. For example, the invention can be realized without means for wetting.

That which is claimed is:

1. An apparatus for determining the mechanical deformation behavior of extrudable measuring samples, comprising a resiliently deflectable mounting frame, two drivable take-up rollers disposed pairwise on said frame and to which an extruded measuring sample billet is supplied, and a drivable guidance device mounted downstream of the take-up rollers in the direction of take-up of the extruded measuring sample billet for actively guiding the extruded measuring sample billet away from the take-up rolls, and means for determining the mechanical deformation of the extruded measuring sample billet from the force exerted on the drivable take-up rollers.

2. The apparatus as claimed in claim 1, further comprising means for synchronizing the driving of the guidance device with the driving of the take-up rollers.

3. The apparatus as claimed in claim 1, wherein the guidance device is mounted on the mounting frame.

4. The apparatus as claimed in claim 1, wherein the guidance device comprises at least two drivable guidance cylinders disposed pairwise on the mounting frame.

5. The apparatus as claimed in claim 4, wherein the guidance cylinders are disposed such that the measuring sample billet is guided between the running surface of the guidance cylinders.

6. The apparatus as claimed in claim 4, wherein the guidance cylinders are disposed such that the measuring sample billet is guided on the front faces of the guidance cylinders.

7. The apparatus as claimed in claim 4, wherein the driving of the guidance cylinders is coupled with the driving of the take-up rollers.

8. The apparatus as claimed in claim 7, wherein the coupling comprises a gearing connection.

9. The apparatus as claimed in claim 7, wherein the transport speed of the guidance cylinders is slightly higher than the transport speed of the take-up rollers.

10. The apparatus as claimed in claim 4, further comprising means for wetting the surfaces of the take-up rollers coming into contact with the measuring sample billet.

11. The apparatus as claimed in claim 10, further comprising means for wetting the surfaces of the guidance cylinders coming into contact with the measuring sample billet.

12. The apparatus as claimed in claim 11, wherein said means for wetting comprises at least one wetting agent reservoir assigned to each take-up roller, and to each guidance cylinder, and wherein each reservoir is in contact with the particular surface to be wetted.

13. The apparatus as claimed in claim 12, wherein each reservoir is in contact with the particular surface to be wetted via a textile structure with absorptive capacity or a small sponge.

14. The apparatus as claimed in claim 12, wherein a highly volatile liquid serves as the wetting agent.

15. The apparatus as claimed in claim 11, further comprising means for detecting the weight loss due to the evaporation of the wetting agent from the surfaces of the take-up rollers and the surfaces of the guidance cylinders.

16. The apparatus as claimed in claim 1 further comprising means mounting the take-up rollers on said mounting frame so as to permit the spacing therebetween to be adjusted.

\* \* \* \* \*